United States Patent
Park et al.

(10) Patent No.: US 12,391,639 B2
(45) Date of Patent: Aug. 19, 2025

(54) MEMBRANE SEPARATION PROCESS FOR SEPARATING CARBONATE-CONTAINING DIAMINOALKANE SOLUTION

(71) Applicant: CJ CHEILJEDANG CORPORATION, Seoul (KR)

(72) Inventors: Ho Bum Park, Seoul (KR); Tae Hoon Lee, Daejeon (KR); Jaehun Lee, Seoul (KR); Young Lyeol Yang, Seoul (KR); Changyub Oh, Seoul (KR); Jung Min Lee, Seoul (KR); Jihyun Shin, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 592 days.

(21) Appl. No.: 17/906,603

(22) PCT Filed: Mar. 10, 2021

(86) PCT No.: PCT/KR2021/002949
§ 371 (c)(1),
(2) Date: Sep. 19, 2022

(87) PCT Pub. No.: WO2021/187796
PCT Pub. Date: Sep. 23, 2021

(65) Prior Publication Data
US 2023/0167049 A1  Jun. 1, 2023

(30) Foreign Application Priority Data
Mar. 19, 2020 (KR) .................. 10-2020-0033955

(51) Int. Cl.
*C07C 209/86* (2006.01)
*B01D 61/22* (2006.01)
(Continued)

(52) U.S. Cl.
CPC ............ *C07C 209/86* (2013.01); *B01D 61/22* (2013.01); *B01D 63/02* (2013.01); *B01D 71/262* (2022.08);
(Continued)

(58) Field of Classification Search
None
See application file for complete search history.

(56) References Cited

U.S. PATENT DOCUMENTS

| 2012/0226258 A1 | 9/2012 | Otto et al. |
| 2017/0369913 A1 | 12/2017 | Suominen et al. |
| 2018/0002272 A1 | 1/2018 | Qin et al. |

FOREIGN PATENT DOCUMENTS

| JP | 2012-188407 A | 10/2012 |
| JP | 2013-500797 | 1/2013 |

(Continued)

OTHER PUBLICATIONS

Wang, Z. et al. Amine-based absorbents selection for CO2 membrane vacuum regeneration technology by combined absorption-desorption analysis. Chemical Engineering Science. 2013, vol. 93, pp. 238-249.

(Continued)

*Primary Examiner* — Renee Claytor
*Assistant Examiner* — Jennifer C Sawyer
(74) *Attorney, Agent, or Firm* — KNOBBE, MARTENS, OLSON & BEAR, LLP

(57) ABSTRACT

A method of removing carbon dioxide from a carbonate-containing diaminoalkane solution, the method including passing the carbonate-containing diaminoalkane solution through a membrane module, and a method of preparing diaminoalkane including the same.

13 Claims, 6 Drawing Sheets

(51) Int. Cl.
    *B01D 63/02*     (2006.01)
    *B01D 71/26*     (2006.01)
    *B01D 71/34*     (2006.01)
    *B01D 71/68*     (2006.01)
    *C07C 211/09*     (2006.01)

(52) U.S. Cl.
    CPC ............. *B01D 71/34* (2013.01); *B01D 71/68* (2013.01); *C07C 211/09* (2013.01); *B01D 2311/04* (2013.01); *B01D 2311/06* (2013.01); *B01D 2311/10* (2013.01); *B01D 2311/14* (2013.01); *B01D 2311/16* (2013.01); *B01D 2311/22* (2013.01); *B01D 2311/2669* (2013.01); *B01D 2311/2688* (2013.01); *B01D 2317/04* (2013.01)

(56) References Cited

FOREIGN PATENT DOCUMENTS

| | | |
|---|---|---|
| KR | 10-2015-0055607 A | 5/2015 |
| KR | 10-2016-0131687 A | 11/2016 |
| KR | 10-2019-0043322 A | 4/2019 |

OTHER PUBLICATIONS

Office Action received in Japanese Patent Application No. 2022-556462, dated Jan. 9, 2024.
Fang, Mengxiang, et al. "CO2 chemical absorption by using membrane vacuum regeneration technology." Energy Procedia 1.1 (2009): 815-822, XP026471955, ISSN: 1876-6102, DOI: 10.1016/J.EGYPR0.2009.01.108 [retrieved on Feb. 1, 2009].
Extended European Search Report received in European Patet Application No. 21771999.6, dated Oct. 5, 2023.

[Figure 1]
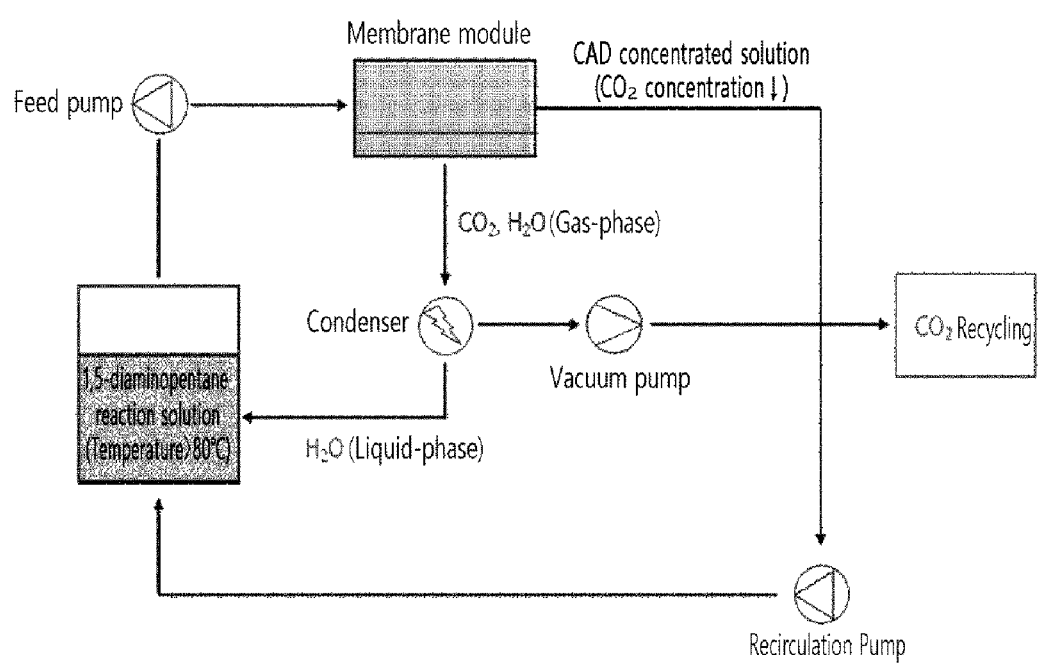

[Figure 2]
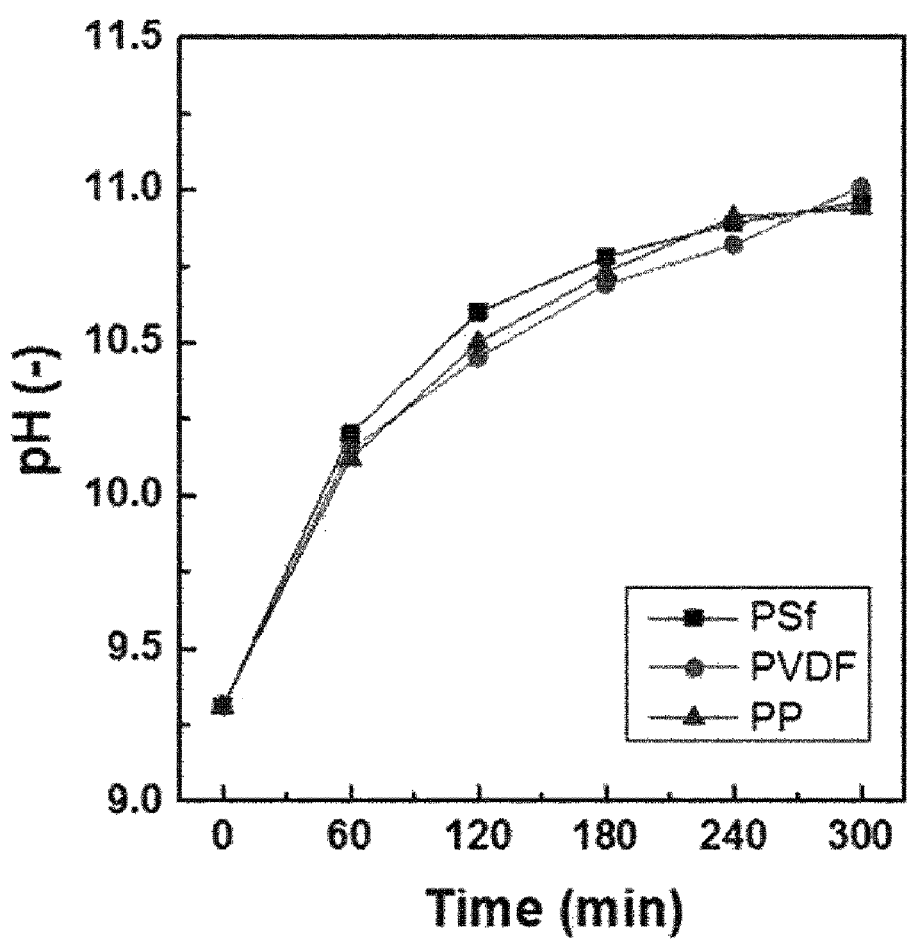

[Figure 3]
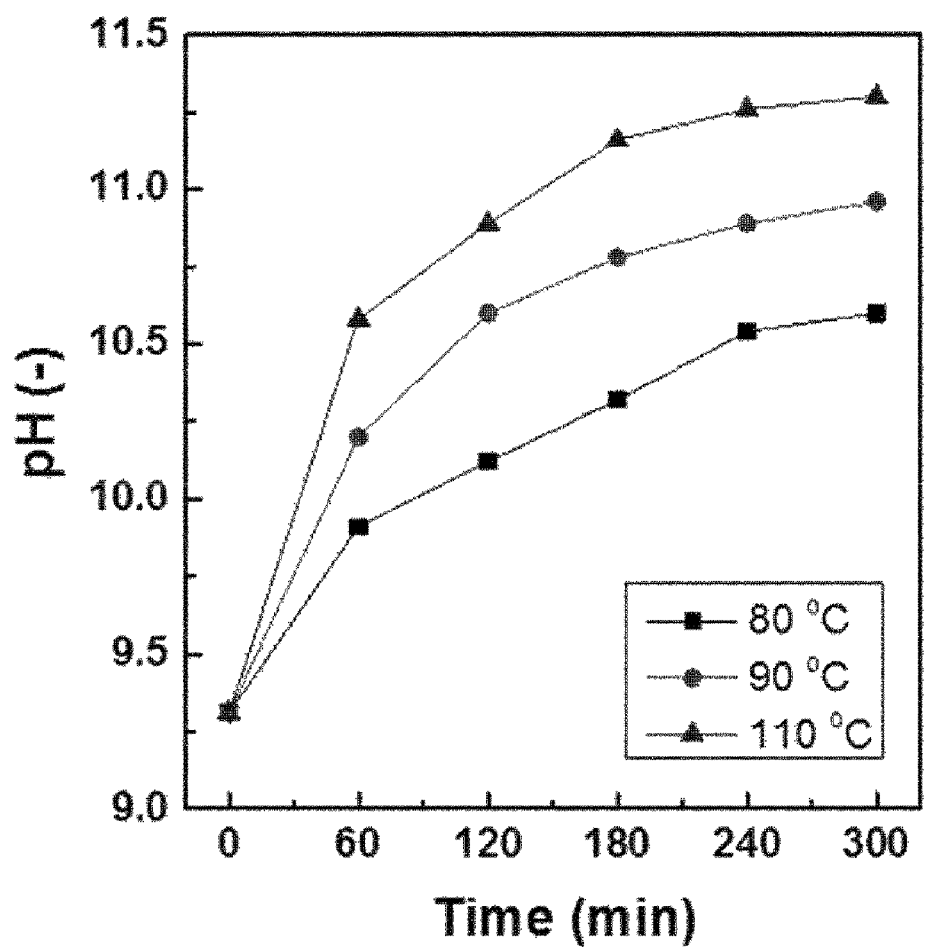

[Figure 4]
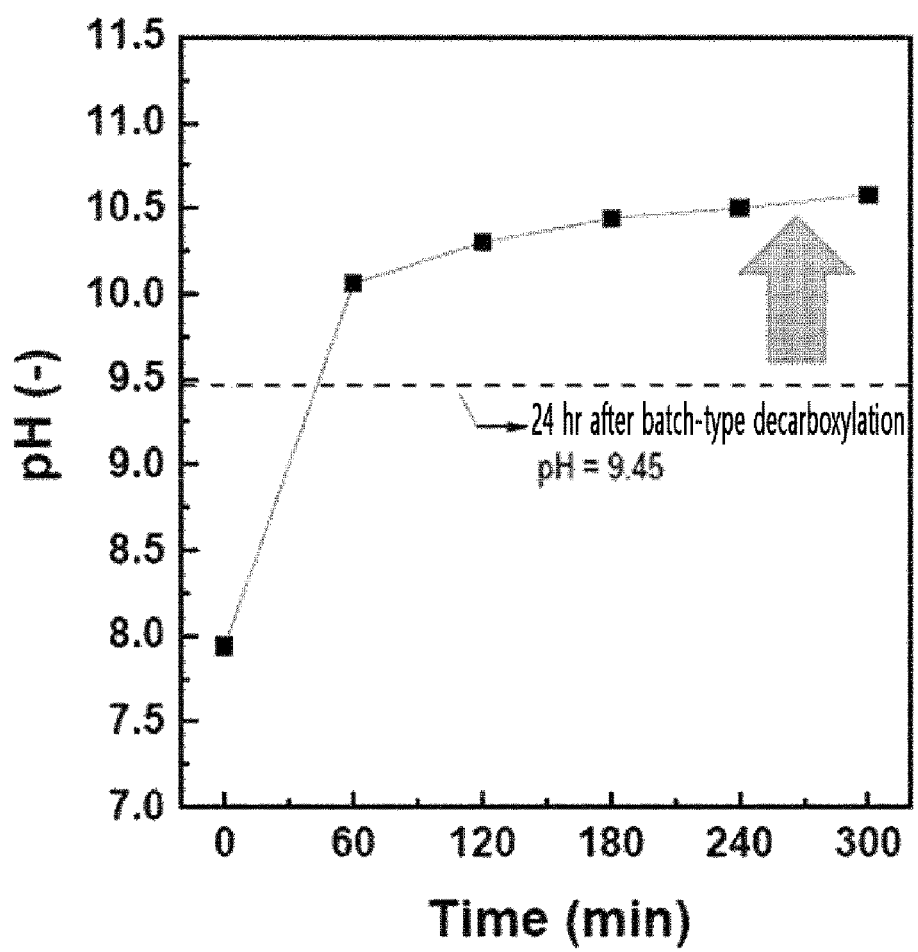

[Figure 5]
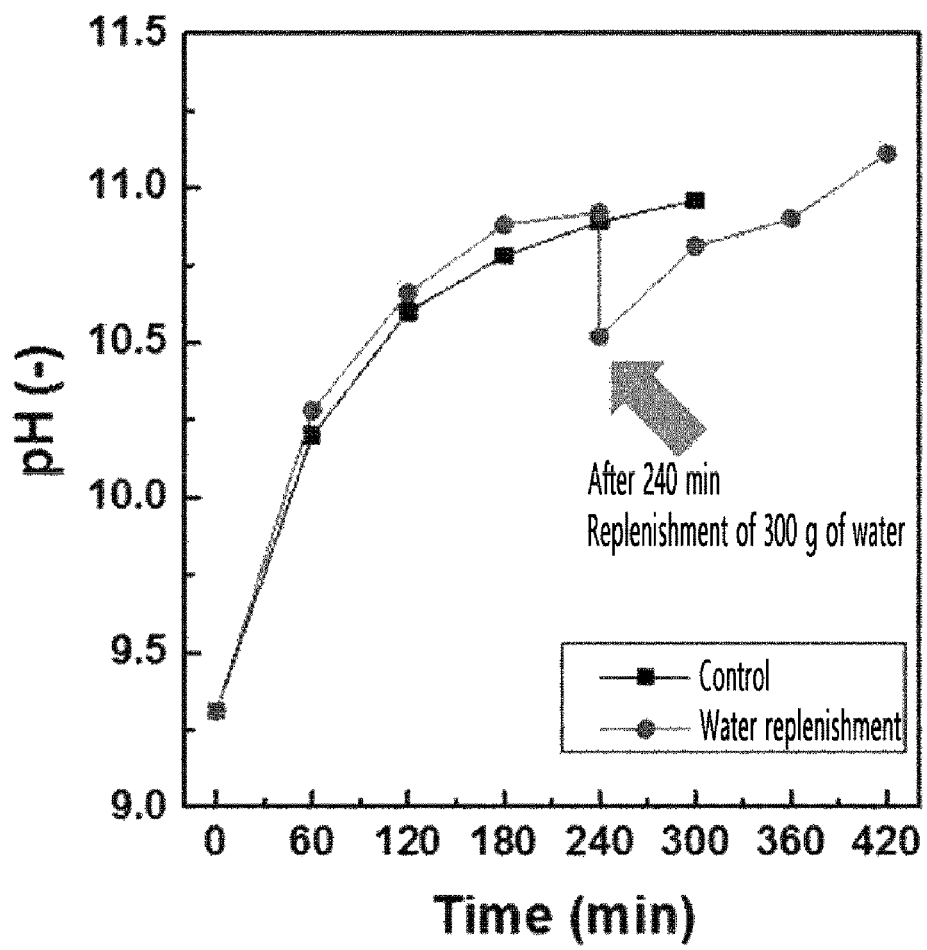

[Figure 6]
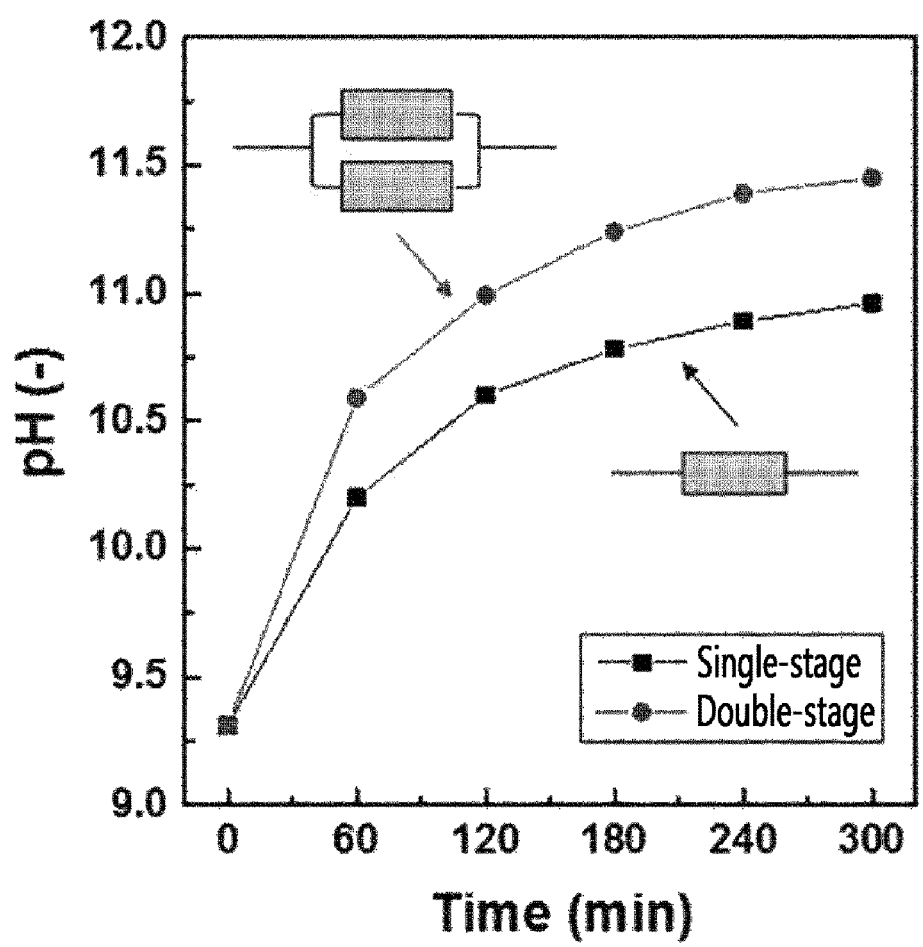

MEMBRANE SEPARATION PROCESS FOR SEPARATING CARBONATE-CONTAINING DIAMINOALKANE SOLUTION

CROSS-REFERENCE TO RELATED APPLICATIONS

This application is a U.S. National Phase Application of PCT International Application No. PCT/KR2021/002949, filed on Mar. 10, 2021, designating the United States of America, which is an International Application of and claims the benefit of priority to Korean Patent Application No. 10-2020-0033955, filed on Mar. 19, 2020, the entire contents of which are incorporated herein by reference.

TECHNICAL FIELD

The present disclosure relates to a method of removing carbon dioxide from a carbonate-containing diaminoalkane solution, the method comprising the step of passing the carbonate-containing diaminoalkane solution through a membrane module, and a method of preparing diaminoalkane comprising the same.

BACKGROUND ART

Among diaminoalkane compounds containing amine groups at both ends of saturated hydrocarbon skeleton, 1,5-diaminopentane, which is a compound called cadaverine, is a diamine-based compound with an unpleasant odor originally produced during putrefaction of animal tissue. However, it is a product of decarboxylation of lysine, which is a kind of amino acid, and has received attention as a raw material for nylon 56, nylon 510, polyurethane, urea, etc. As another example, 1,4-diaminobutane, which is a compound called putrescine, is also an organic compound with an unpleasant odor produced during a decomposition process of amino acids, and is used as a monomer for the preparation of polymers such as polyamines, etc. As still another example, 1,6-diaminohexane, also called hexamethylenediamine (HMD or HMDA), is an organic compound with a strong amine odor, and is an important raw material in the chemical industry for the preparation of polyamides, polyureas, or polyurethanes, and copolymers thereof. Meanwhile, these diaminoalkanes may be obtained in the form of a salt, such as sulfate and carbonate, according to the preparation method. For example, 1,5-pentanediamine adipate may be recovered as a crystal by adding adipic acid to a sulfate of 1,5-diaminopentane. Alternatively, a carbonate of 1,5-diaminopentane may be directly recovered as a crystal. However, the above preparation methods have low yields, and due to the presence of carbonate as a reaction by-product, the product is obtained in the form of a salt, when the carbonate is not removed. Thus, in order to remove the salt and to obtain pure diaminoalkane, an additional separation/purification process is required, which incurs additional costs. Therefore, in order to reduce production costs, there is a need for a method capable of directly and effectively purifying diaminoalkane by simply and efficiently removing carbonate ions from a reaction solution.

However, the existing diaminoalkane purification process has required additional additives for pH control, etc. Accordingly, an additional process of separating the additives is required, or problems may arise, such as formation of impurities and/or scale generation inside a reactor due to the additives, etc.

On the other hand, a membrane separation process has advantages of low energy consumption, simple process, no need for additives, and easy scale-up, and thus many studies and demonstrations have been conducted on replacement of the existing separation process and improvement of reactor efficiency.

DISCLOSURE

Technical Problem

The present inventors have made many efforts to develop a process capable of efficiently removing carbonate from a reaction solution of a diaminoalkane, based on the existing distillation separation process, and as a result, they found that when a membrane contactor separation process of using a polymer membrane is combined prior to a decarboxylation step by distillation, it is possible to more efficiently remove carbonate at a relatively low temperature, thereby completing the present disclosure.

Technical Solution

An object of the present disclosure is to provide a method of removing carbon dioxide from a carbonate-containing diaminoalkane solution, the method comprising the step of passing the carbonate-containing diaminoalkane solution through a membrane module.

Another object of the present disclosure is to provide a method of preparing diaminoalkane, the method comprising the step of separating diaminoalkane from the solution, from which carbon dioxide is removed according to the above method.

Advantageous Effects

According to a method of the present disclosure, since a primary decarboxylation process of using a membrane module is combined prior to a secondary decarboxylation process of removing carbon dioxide through distillation, an efficient decarboxylation process is possible in an energy-efficient manner at a relatively low temperature through the primary decarboxylation process, and thus the burden in the secondary decarboxylation process may be significantly reduced. Therefore, problems, such as poor mass transfer performance due to the low gas-liquid contact area generated in the carbon dioxide removal process by simple distillation and consequent scale-up of equipment, corrosion of equipment, solvent loss, overflow, foam, drift, entrainment, etc., do not arise. Furthermore, in the process of using the membrane module, no additives are used, and thus it does not require an additional process of separating the additives. Accordingly, it may be expected to improve the economic feasibility and efficiency of the process.

DESCRIPTION OF DRAWINGS

FIG. 1 shows a schematic illustration of a reactor configuration for a membrane separation process according to one exemplary embodiment of the present invention;

FIG. 2 shows pH changes in a 1,5-diaminopentane-containing reaction solution according to materials of the membrane module and operation time according to one exemplary embodiment of the present invention;

FIG. 3 shows pH changes in the 1,5-diaminopentane-containing reaction solution according to temperature during operation of a membrane module made of PSf according to one exemplary embodiment of the present invention;

FIG. 4 shows pH changes in a 1,4-diaminobutane-containing reaction solution over time of the membrane separation process according to one exemplary embodiment of the present invention;

FIG. 5 shows effects of viscosity control during operation of the membrane module according to one exemplary embodiment of the present invention; and FIG. 6 shows effects of a configuration of a multiple-stage membrane module on pH changes of the reaction solution over the operation time according to one exemplary embodiment of the present invention.

BEST MODE

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

To achieve the above objects, one aspect of the present disclosure provides a method of removing carbon dioxide from a carbonate-containing diaminoalkane solution, the method comprising the step of passing the carbonate-containing diaminoalkane solution through a membrane module.

With regard to the method of the present disclosure, it is possible to provide pure free diaminoalkane not in the form of carbonate by removing 1 equivalent or more of carbon dioxide through the above process.

To this end, the process may be performed in combination with an additional process of purifying diaminoalkane, but is not limited thereto. For example, the step of distilling the reaction solution obtained from the above process may be additionally performed to remove excess carbon dioxide present in the reaction solution, thereby providing diaminoalkane with higher purity, but is not limited thereto. The process may be performed in combination with other methods of purifying diaminoalkane, which are known to those skilled in the art.

In addition, the method of the present disclosure may further comprise the step of preparing a carbonate-containing diaminoalkane solution as a raw material, prior to performing the process of removing carbon dioxide using the membrane module, but is not limited thereto.

For example, the step of preparing the carbonate-containing diaminoalkane solution may be performed through microbial fermentation, biological conversion, or both of the processes, but is not limited thereto.

With regard to the method of the present disclosure, the diaminoalkane may be 1,4-diaminobutane, 1,5-diaminopentane, or 1,6-diaminohexane, but is not limited thereto.

For example, the 1,5-diaminopentane may be produced by the decarboxylation reaction of lysine, specifically by culturing a microorganism to produce lysine, followed by an enzyme conversion reaction of the culture using decarboxylase or using a microorganism into which the enzyme is introduced. Alternatively, a 1,5-diaminopentane-producing microorganism is prepared by introducing decarboxylase to a lysine-producing microorganism, and a 1,5-diaminopentane solution may be obtained by culturing the microorganism. In addition, the 1,5-diaminopentane solution may also be obtained by various known methods. Similarly, a 1,4-diaminobutane or 1,6-diaminohexane solution may also be prepared by culturing a 1,4-diaminobutane-producing microorganism or a 1,6-diaminohexane-producing microorganism, and various known methods may also be used. As described above, the diaminoalkane solutions prepared by microbial fermentation or enzymatic conversion may contain carbonate.

For example, it was confirmed that decarboxylation with excellent efficiency is possible under a lower temperature condition than that in the decarboxylation by simple heating by applying the method of the present disclosure to cadaverine, i.e., 1,5-diaminopentane, which is a representative material of diaminoalkanes, and furthermore, the similar pattern of decarboxylation is also possible for 1,4-diaminobutane. Since 1,4-diaminobutane, 1,5-diaminopentane, and 1,6-diaminohexane are all known to have similar carbon dioxide adsorption/desorption properties, the method of the present disclosure may be applied to all of these materials.

As used herein, the term "membrane module" refers to a complete unit consisting of a (separative) membrane, a housing, a feed inlet, a concentrate outlet, and a permeate outlet. The membrane module may comprise a variety of membrane configurations including, but not limited to, hollow fiber, flat sheet, or tubular membrane.

The membrane module applicable to the method of the present disclosure is preferably provided with a porous and hydrophobic polymer membrane as a (separative) membrane. The membrane may comprise a hollow fiber membrane made of polysulfone (PSf), polyvinylidene fluoride (PVDF), or polypropylene (PP), but is not limited thereto.

For example, decarboxylation may be performed under the same operation conditions using a membrane module provided with hollow fiber membranes of different specifications made of the three types of polymers. In addition, by comparing the results, decarboxylation with similar pattern and performance may be performed, regardless of the material of the membrane. This indicates that the rate-determining step in the decarboxylation is dominated by the slow reaction rate at which the bond between diaminoalkane and carbon dioxide is broken, rather than the mass transfer resistance of the membrane. Therefore, since the type of polymer in constituting the membrane module does not significantly influence the decarboxylation performance, the characteristics of the materials are not limited, and the polymer may be selected from a wide range in consideration of stability under operation conditions.

With regard to the method of the present disclosure, the step of passing the solution through the membrane module may be performed by feeding the reaction solution at a flow rate of 10 cm/s to 60 cm/s. For example, the step may be performed by feeding the reaction solution at a flow rate of 15 cm/s to 55 cm/s, more specifically 20 cm/s to 55 cm/s, 30 cm/s to 55 cm/s or 32 cm/s to 53 cm/s, but is not limited thereto. For example, when the flow rate of the feed is lower than 10 cm/s, it may be difficult to achieve the desired level of decarboxylation efficiency within the desired time, due to the delayed reaction. When the flow rate is higher than 60 cm/s, there is a possibility that the membrane is overloaded to decrease the decarboxylation efficiency or to impair the durability of the membrane.

With regard to the method of the present disclosure, the step of passing the solution through the membrane module may be performed at a pressure difference of 1 bar to 3 bar, but is not limited thereto. The pressure difference may be achieved by applying a pressure to the feed reaction solution from the top of the membrane module. For example, the step may be performed at a pressure difference of 1.2 bar to 3 bar, more specifically 1 bar to 2.5 bar, 1.2 bar to 2.5 bar, or 2 bar to 2.5 bar, but is not limited thereto. For example, when the pressure difference is too low, the mass transfer rate is slow due to insufficient driving force, and thus the reaction efficiency may be reduced. On the contrary, as the pressure difference is higher, the higher decarboxylation efficiency may be expected. However, the membrane is strained by the high pressure difference to decrease the durability of the membrane and to impair the long-term stability, and an additional equipment, such as a pump, etc., is needed to add the pressure difference, which may incur an economic burden.

Alternatively, decarboxylation may be induced by applying a vacuum of $1\times10^3$ Torr to $1\times10^2$ Torr to the lower portion of the membrane module, but is not limited thereto.

With regard to the method of the present disclosure, the step of passing the solution through the membrane module may be performed at 80° C. to 110° C. For example, the step of passing through the membrane module may be performed at 85° C. to 110° C., specifically 85° C. to 100° C., more specifically 87° C. to 95° C., but is not limited thereto. When the operation temperature is lower than 80° C., decarboxylation may be incomplete, and thus sufficient carbon dioxide removal may not be achieved. When operated at a high temperature exceeding 110° C., it not only causes excessive energy consumption, but also causes defects by wetting the membrane and/or damaging the polymer membrane itself.

With regard to the method of the present disclosure, the step of passing the solution through the membrane module may be performed for 30 minutes to 10 hours. For example, the step of passing through the membrane module may be performed for 60 minutes to 8 hours, specifically 1 hour to 5 hours, more specifically 2 hours to 5 hours, or 3 hours to 5 hours, but is not limited thereto. For example, when the reaction time is short, less than 30 minutes, the carbon dioxide may not be removed to the desired level, because a sufficient reaction does not occur. When the reaction time exceeds 10 hours, additional decarboxylation does not occur after a certain period of time, and thus unnecessary time and/or energy consumption may be involved.

The method of the present disclosure is characterized in that pH of the reaction solution increases to 10 or higher, specifically to 10.5 or higher, after the process of removing carbon dioxide. The increase in pH of the reaction solution indicates that carbon dioxide has been removed from the reaction solution. Through the step of passing through the membrane module, in which the membrane module is employed, carbon dioxide corresponding to 1 equivalent may be removed, and as a result, the reaction solution may have a pH value of 10 or higher.

With regard to the method of the present disclosure, the step of passing the solution through the membrane module may further comprise a step of adding water during the step. The first step is performed at an elevated temperature of 80° C. or higher. Therefore, water vapor, which is a gas generated by evaporation of water contained in the reaction solution, is removed together with carbon dioxide, and viscosity of the reaction solution increases overtime, and accordingly, the mass transfer may be lowered and the reaction rate may be lowered. In order to solve this problem, water may be additionally supplied to the reaction solution during the reaction so as to facilitate the mass transfer by lowering the viscosity of the reaction solution. With regard to the supplied water, water vapor which is separated from the reaction solution by evaporation may be condensed and then re-injected into the reaction solution, but is not limited thereto.

For example, the pH increase rate decreases and approaches a certain level over the operation time, but when water is re-supplied 4 hours after the start of the operation, the pH sharply rises again, and it also continues to increase over time even after 7 hours.

With regard to the method of the present disclosure, the membrane module may be provided with two or more (separative) membranes which are connected to each other in parallel in order to increase the membrane contact surface. The membrane contact surface may be one factor determining the decarboxylation efficiency.

For example, when a module constructed by simply connecting two membranes in parallel is used, much superior decarboxylation performance may be achieved under the same conditions. This indicates that the module may be applied to large-scale production by extending the reaction scale by the simple method of connecting membranes in parallel, as well as improving the performance.

With regard to the method of the present disclosure, the step of distilling the solution to remove residual carbonate, the step of removing impurities in the solution, or both of the steps may be further performed, after the step of passing the solution through the membrane module. Through the additional processes, it is possible to provide diaminoalkane with higher purity. At this time, the process of removing impurities may also be performed by using a distillation method, but is not limited thereto, and the process may be performed using a method known in the art without limitation.

Another aspect of the present disclosure provides a method of preparing diaminoalkane, the method comprising the step of separating diaminoalkane from the solution, from which carbon dioxide is removed according to the above-described method.

With regard to the method of preparing diaminoalkane according to the present disclosure, the step of separating diaminoalkane may be performed using a method of separating and/or purifying diaminoalkane known in the art without limitation.

MODE FOR INVENTION

Hereinafter, the present disclosure will be described in more detail with reference to the following exemplary embodiments. However, the following exemplary embodiments are for illustrative purposes only, and the scope of the present disclosure is not intended to be limited by these exemplary embodiments.

Preparation Example 1: Preparation of Carbonate-Containing 1,6-Diaminopentane Solution by Microbial Fermentation and Enzymatic Conversion Reaction A fermentation broth containing L-lysine was prepared by culturing an L-lysine-producing microorganism. Cells were removed from the fermentation broth, and a 1,5-diaminopentane-containing solution was prepared through an enzymatic conversion reaction. At this time, the solution was confirmed to contain 40% to 60% of carbonate.

Example 1: Selection of Membrane Material and Module

A membrane material for efficient decarboxylation of the 1,5-diaminopentane reaction solution requires high porosity, hydrophobicity, and thermal and chemical stability. As candidates for the material, polysulfone (PSf)-, polyvinylidene fluoride (PVDF)-, and polypropylene (PP)-based hollow fiber modules were prepared. The main characteristics of each membrane module are summarized in Table 1 below.

TABLE 1

|  | 1 | 2 | 3 |
|---|---|---|---|
| Material | PSf | PVDF | PP |
| Module size (diameter/length, cm/cm) | 7.7/28 | 3.8/35 | 4/65 |
| Membrane area (m$^2$) | 1.2 | 1.0 | 0.2 |
| Carbon dioxide permeability (GPU) | 200,000 | 500 | 100,000 |

*GPU = gas permeation unit, $$1 \text{ GPU} = 10^{-6} \frac{\text{cm}^3 (\text{STP})}{\text{cm}^2 \times \text{s} \times \text{cmHG}}$$

Example 2: Decarboxylation Performance According to Membrane Material and Operation Conditions pH of the reaction solution is an indirect indicator that determines the amount of carbonate ions remaining in the solution. An increase in pH of the solution according to the reaction indicates a decrease in carbonate ions in the solution, that is, the removal of carbonate ions by the reaction. Therefore, higher pH of the reaction solution after the decarboxylation process indicates better decarboxylation performance. 1,000 g of the 1,5-diaminopentane reaction solution prepared from the lysine fermentation broth (initial pH of the reaction solution=8.30) was put into a flask, and each membrane module was connected, and pH was measured after reacting for a predetermined time under each condition by varying the feed flow rate, pressure difference, and operation temperature. The respective operation conditions and the measured results are shown in Table 2 below. The structure of the reaction apparatus used at this time is schematically shown in FIG. 1.

TABLE 2

| Module | Feed flow rate (cm/s) | Pressure difference (bar) | Operation time (h) | Operation temperature (° C.) | pH after decarboxylation |
|---|---|---|---|---|---|
| PSf | 32 | 1.2 | 4 | 80 | 10.60 |
| PSf | 32 | 1.2 | 4 | 90 | 10.86 |
| PSf | 53 | 2.4 | 5 | 90 | 10.96 |
| PSf | 53 | 2.4 | 5 | 110 | 11.30 |
| PSf (double-stage) | 53 | 2.4 | 5 | 90 | 11.45 |
| PVDF | 32 | 1.2 | 5 | 90 | 10.90 |
| PVDF | 53 | 2.4 | 5 | 90 | 11.01 |
| PP | 4 | 1.2 | 5 | 80 | 9.87 |
| PP | 16 | 1.2 | 5 | 80 | 10.20 |
| PP | 32 | 1.2 | 5 | 80 | 10.75 |
| PP | 53 | 2.4 | 5 | 90 | 10.94 |

As shown in Table 2, when the membrane module of each material was used, the pH of the reaction solution after decarboxylation was increased with the increasing feed flow rate, pressure difference, and operation temperature. This indicates that the mass transfer between the liquid phase and the gas phase increased with the increasing feed flow rate, pressure difference, and operation temperature. Meanwhile, under the same operation conditions (feed flow rate of 53 cm/s, pressure difference of 2.4 bar, operation time of 5 hours, and operation temperature of 90° C.), the similar decarboxylation effects, that is, similar pH values, were exhibited (10.96, 11.01, and 10.94 for PSf, PVDF, and PP, respectively), regardless of the membrane material, indicating that the rate-determining step in the decarboxylation is dominated by the slow reaction rate at which the bond between 1,5-diaminopentane and carbon dioxide is broken, rather than the mass transfer resistance of the membrane. The same trend was also observed over time. As shown in FIG. 3, the pH of the reaction solution increased over the reaction time, and under the same operation time and conditions, the similar values were shown regardless of the material of the membrane module.

Example 3: Decarboxylation Performance According to Operation Temperature During Operation of Membrane Module Made of PSf As shown in Example 2, all of the tested membrane modules showed similar decarboxylation performance under the same conditions without the influence of materials. Therefore, the membrane module made of PSf, which has the highest glass transition temperature (Tg) to have excellent thermal stability, among the materials, was used to evaluate the decarboxylation performance according to temperature. In a specific experiment, pH was measured every hour while the reaction was allowed for up to 5 hours under operating conditions of a feed flow rate of 53 cm/s and a pressure difference of 2.4 bar at different temperatures, and the results are shown in FIG. 3.

As shown in FIG. 3, pH increased as the operation time increased under all temperature conditions. As the operation temperature was higher, pH was the higher at the same reaction time, indicating better decarboxylation performance. However, when operated at an excessive high temperature for a long time, incidental problems may occur, such as a membrane wetting phenomenon and/or generation of defects in the membrane module. Therefore, it is necessary to achieve the desired decarboxylation performance by controlling the operation time at an appropriate temperature. For example, referring to FIG. 3, the reaction solution reacted at 90° C. for 4 hours showed similar pH to the reaction solution reacted at 110° C. for 2 hours, indicating that it is possible to achieve the desired level of decarboxylation performance by appropriately controlling the operation temperature and time.

Example 4: Decarboxylation Performance According to Type of Diaminoalkane in Reaction Solution Decarboxylation performance according to temperature was evaluated by applying the membrane module made of PSf to a reaction solution, in which carbon dioxide was dissolved, containing 1,4-diaminobutane instead of 1,5-diaminopentane. Specifically, pH was measured every hour while the reaction was allowed for up to 5 hours under operating conditions of a feed flow rate of 53 cm/s and a pressure difference of 1.2 bar at 90° C., and the results are shown in FIG. 4.

As shown in FIG. 4, pH of the reaction solution rapidly increased to 10 or more within 1 hour after the start of the reaction. This indicates the similar level of decarboxylation performance, as compared to the results for 1,5-diaminopentane as shown in FIG. 3, and indicates that the process of removing carbonate using the membrane module of the present disclosure may be applied, regardless of the type of diaminealkane.

Example 5: Effect of Viscosity Control During Operation

Decarboxylation by the membrane module is performed at a high temperature close to 100° C. Thus, as the operation time increases, not only carbon dioxide but also some water evaporates, which is also removed together in the form of water vapor, leading to an increase in the viscosity of the reaction solution and a decrease in the decarboxylation efficiency. In order to solve this, after a predetermined time, the step of replenishing the reaction solution with water was further performed, and pH changes were observed while the reaction was continuously performed, and the results are shown in FIG. 5.

As shown in FIG. 5, when operated under the same conditions (feed flow rate of 53 cm/s, pressure difference of 2.4 bar, operation temperature of 90° C.), the pH increase rate, which decreased over time, showed a rapid recovery when replenishing water after 4 hours of reaction, and pH continued to increase even when the operation time was extended up to 7 hours. It is considered that this is because the viscosity of the reaction solution was lowered by water replenishment, and accordingly, the mass transfer was facilitated. In this regard, water for replenishment may be re-supplied by cooling the water vapor discharged by evaporation from the reaction solution.

Example 6: Decarboxylation Performance According to Configuration of Double-Stage Parallel Membranes Made of PSf The effect of increasing the contact surface on decarboxylation performance was evaluated by using the same two PSf membrane modules which were connected in parallel in two stages. The evaluation was performed under conditions of a feed flow rate of 53 cm/s, a pressure difference of 2.4 bar, and an operation temperature of 90° C. for 5 hours, and pH was measured every hour, and the results are shown in FIG. 6.

As shown in FIG. 6, it was confirmed that pH of the reaction solution may be increased within a shorter time when using the double-stage membrane module connected in parallel, as compared to the case of using a single-stage membrane module. This indicates that the separation process may be scaled up or the efficiency improved by way of the simple method of connecting in parallel.

Comparative Example 1: Decarboxylation Process Via Simple Temperature Increase In order to compare the decarboxylation performances between a simple batch-type system and the membrane separation process, 1,000 g of a 1,5-diaminopentane reaction solution was placed in a flask, and it was simply heated to 90° C. without connection with a membrane contactor. While maintaining up to 24 hours, pH of the reaction solution was measured at the time points of 5 hours and 24 hours, and as a result, pH values of 9.90 and 10.15 were measured, respectively. This is because the decarboxylation process of using the membrane module of the present disclosure exhibited better decarboxylation performance at the same operation temperature and operation time (when operated using the PSf, PVDF, and PP membranes for 5 hours under the same conditions, pH of the reaction solution was 10.96, 11.01 and 10.94, respectively), as compared to the simple batch-type decarboxylation system, an equivalent or higher decarboxylation effect may be achieved at a lower feed flow rate, a lower pressure difference, a lower operating temperature, and/or a shorter operation time, indicating that the energy-efficient process is possible.

In order to more specifically calculate a decarboxylation rate and a mass balance as well as the pH change during the decarboxylation process, the reaction solution after decarboxylation was quantitatively analyzed by liquid chromatography, and the results are shown in Table 3 below. In Table 3, the results of performing the batch-type decarboxylation process of Comparative Example 1 for 24 hours were compared with the results of Cases 1 to 3 of performing the decarboxylation process for 5 hours using the PP module according to Examples while varying the feed flow rate, pressure difference, and/or operation temperature. As shown in Table 3 below, when the membrane modules were used, the loss of 1,5-diaminopentane and/or the residual amount of carbonate were/was reduced, and a significantly higher decarboxylation rate of 2.8 times to 3.7 times were observed, even when performed for a short operation time of about ⅕ at an equal or lower operation temperature, as compared to the batch system.

TABLE 3

| Example | 1,5-Diaminopentane reaction solution (Feed) | Case 1 | Case 2 | Case 3 | Comparative Example 1 (batch type) |
|---|---|---|---|---|---|
| pH | 8.30 | 9.87 | 10.20 | 10.94 | 10.15 |
| Loss of 1,5-diaminopentane (%) | — | 0.2 | 0.1 | 0.0 | 0.2 |
| Water (KF) | 45.4 | 49.5 | 48.9 | 43.8 | 56.1 |
| Residual amount of carbonate ($HCO_3^-$/1,5-diaminopentane, wt %) | 74.1 | 67.6 | 66.5 | 65.6 | 71.8 |
| Decarboxylation rate (%) | — | 8.7 | 10.2 | 11.4 | 3.1 |

Case 1: PP module, Feed of 4 cm/s, pressure difference of 1.2 bar, operation time of 5 h, operation temperature of 80° C.,
Case 2: PP module, Feed of 16 cm/s, pressure difference of 1.2 bar, operation time of 5 h, operation temperature of 80° C.,
Case 3: PP module, Feed of 53 cm/s, pressure difference of 2.4 bar, operation time of 5 h, operation temperature of 90° C.,
Comparative Example 1: Batch-type decarboxylation, operation time of 24 h, operation temperature of 90° C.

Based on the above description, it will be understood by those skilled in the art that the present disclosure may be implemented in a different specific form without changing the technical spirit or essential characteristics thereof. In this regard, it should be understood that the above embodiment is not limitative, but illustrative in all aspects. The scope of the disclosure is defined by the appended claims rather than by the description preceding them, and therefore all changes and modifications that fall within metes and bounds of the claims or equivalents of such metes and bounds are therefore intended to be embraced by the claims.

The invention claimed is:

1. A method of removing carbon dioxide from a carbonate-containing diaminoalkane solution, the method comprising passing the carbonate-containing diaminoalkane solution through a membrane module, wherein the membrane module is a hollow fiber membrane made of polysulfone (PSf), polyvinylidene fluoride (PVDF), or polypropylene (PP), thereby removing carbon dioxide from the carbonate-containing diaminoalkane solution.

2. The method of claim 1, wherein the carbonate-containing diaminoalkane solution is prepared by microbial fermentation and/or biological conversion.

3. The method of claim 1, wherein the diaminoalkane is 1,4-diaminobutane, 1,5-diaminopentane, or 1,6-diaminohexane.

4. The method of claim 1, wherein passing the solution through the membrane module is performed by feeding the solution at a flow rate of 10 cm/s to 60 cm/s.

5. The method of claim 1, wherein passing the solution through the membrane module is performed at a pressure difference of 1 bar to 3 bar.

6. The method of claim 1, wherein passing the solution through the membrane module is performed by applying a vacuum of $1\times10^3$ Torr to $1\times10^2$ Torr to the lower portion of the membrane module.

7. The method of claim 1, wherein passing the solution through the membrane module is performed at 80° C. to 110° C.

8. The method of claim 1, wherein passing the solution through the membrane module is performed for 30 minutes to 10 hours.

9. The method of claim 1, wherein pH of the solution increases to 10 or higher after passing the solution through the membrane module.

10. The method of claim 1, wherein water is added while passing the solution through the membrane module.

11. The method of claim 1, wherein the membrane module is provided with two or more membranes which are connected to each other in parallel.

12. The method of claim 1, further comprising distilling the solution to remove residual carbonate and/or removing impurities in the solution after passing the solution through the membrane module.

13. A method of preparing diaminoalkane comprising removing carbon dioxide from a carbonate containing diaminoalkane solution, according to the method of claim 1.

* * * * *